(12) United States Patent
Moretti et al.

(10) Patent No.: US 7,704,933 B2
(45) Date of Patent: Apr. 27, 2010

(54) α-DECALONES WITH DAMASCONE-WOODY ODOR

(75) Inventors: Robert Moretti, Grand-Lancy (CH); Olivier Etter, Chene-Bourg (CH)

(73) Assignee: Firmenich SA, Geneva (CH)

( * ) Notice: Subject to any disclaimer, the term of this patent is extended or adjusted under 35 U.S.C. 154(b) by 201 days.

(21) Appl. No.: 11/996,924

(22) PCT Filed: Sep. 5, 2006

(86) PCT No.: PCT/IB2006/053113

§ 371 (c)(1),
(2), (4) Date: Jan. 25, 2008

(87) PCT Pub. No.: WO2007/031904

PCT Pub. Date: Mar. 22, 2007

(65) Prior Publication Data

US 2008/0214433 A1        Sep. 4, 2008

(30) Foreign Application Priority Data

Sep. 15, 2005    (WO) ................. PCT/IB2005/053040

(51) Int. Cl.
*C11D 3/50*    (2006.01)

(52) U.S. Cl. ................... 510/104; 512/15; 568/374
(58) Field of Classification Search ........... 510/104; 512/15; 568/374
See application file for complete search history.

(56) References Cited

U.S. PATENT DOCUMENTS

| 4,320,772 | A | * | 3/1982 | Yoshida | ................... 131/276 |
| 4,339,467 | A | * | 7/1982 | Yoshida | ................... 426/538 |
| 4,377,714 | A | * | 3/1983 | Yoshida | ................... 568/819 |
| 4,387,048 | A |   | 6/1983 | Yoshida | ................... 252/522 |
| 5,114,915 | A |   | 5/1992 | Fehr et al. | ................ 512/15 |

OTHER PUBLICATIONS

International Search Report PCT/IB2006/053113.

* cited by examiner

*Primary Examiner*—John R Hardee
(74) *Attorney, Agent, or Firm*—Winston & Strawn LLP

(57) ABSTRACT

The present invention relates to a new class of compound, α-decalones with a 2,3,8a-trimethyl substitution, which are valuable perfuming ingredients of the woody type. The present invention also concerns the use of these compounds in the perfumery industry as well as the compositions or articles containing these compounds.

13 Claims, No Drawings

α-DECALONES WITH DAMASCONE-WOODY ODOR

This application is a 371 filing of International Patent Application PCT/IB2006/053113 filed on 5 Sep. 2006.

TECHNICAL FIELD

The present invention relates to the field of perfumery. More particularly, it concerns a new class of compounds, α-decalones with a 2,3,8a-trimethyl substitution. Said compounds are valuable woody odorants.

The present invention concerns the use of said compounds in the perfumery industry as well as the compositions or articles containing said compounds.

PRIOR ART

To the best of our knowledge, none of the present compounds is known in the prior art. Their closest analogues, having an interest in perfumery, are the α-decalones with a 2,2,8a-trimethyl substitution (i.e a geminal substitution instead of a vicinal one) and are reported in Table 1 of U.S. Pat. No. 4,377,714. However, in this prior art document there is no suggestion of any organoleptic properties of the compounds of formula (I), or any use of said compounds in the field of perfumery.

Furthermore the odor of these prior art compounds is quite different from the one of the present invention (see below), lending thus the invention's compounds and the prior art compounds to be each suitable for different uses, i.e. to impart different organoleptic impressions.

DESCRIPTION OF THE INVENTION

We have now surprisingly discovered that a compound of formula (I)

wherein the dotted line represents a single or double bond, $R^1$ represents a methyl group or a hydrogen atom and $R^2$ represents a methyl group or a hydrogen atom;

can be used as perfuming ingredient, for instance to impart woody odor, together with other odor notes.

According to a particular embodiment of the invention, the compounds of formula (II)

wherein the dotted line represents a single or double bond and one $R^2$ is a hydrogen atom and the other is a hydrogen atom or a methyl group;

are particularly appreciated.

According to a further embodiment of the invention, the compounds of formula (III)

wherein the dotted line represents a single or double bond; are also particularly appreciated.

Yet, according to a particular embodiment of the invention, the perhydro-2,3,8a-trimethyl-1-naphthalenone, i.e. the compound wherein the dotted line represents a single bond, is particularly appreciated by the perfumers.

Said compound possesses a woody note, of the vetiver type, characterized by a damascone and ionone connotation and possessing also a well perceivable watery connotation. The odor of this invention's compound is considered by the perfumers as quite unique for a synthetic compound as it marries a woody/vetiver type note, quite rare itself, with damascone-violette and watery notes providing thus a unique odor profile.

When the odor of this invention's compound is compared with the one of the closest prior art compound, perhydro-2, 3,8a-trimethyl-1-naphthalenone (see the document cited above), then the invention's compound distinguishes itself by lack of at least the sweet-fruity, minty and camphor notes which are the main odor descriptors of the odor of its prior art analogue. Furthermore the prior art compound lacks the woody-damascone character and note so typical of the invention's compound. In other works the two compounds possess different odors which lend the invention's compounds and the prior art compounds to be each suitable for different uses, i.e. to impart different organolpetic impressions.

The other invention's compound is the 2,3,8a-trimethyl-3, 4,4a,5,8,8a-hexahydro-1(2H)-naphthalenone. Said compound possesses also a woody note, of the agarwood type. The organoleptic properties of this compound differ from the ones of its closest analogue, i.e 2,2,8a-trimethyl-3,4,4a,5,8, 8a-hexahydro-1(2H)-naphthalenone (U.S. Pat. No. 4,377,714), by lacking the minty, camphor and citrus notes which are the main odor descriptors of the odor of its prior art analogue.

Therefore, the present compounds of formula (III) possess different and unexpected odors from the ones of their prior art closest structural analogues.

As other examples of the invention's compounds one may cite, for example, 2,3,6,8a-tetramethyl-3,4,4a,5,8,8a-hexahydro-1(2H)-naphthalenone which has a woody, ambery, patchouli odor and distinguishes itself from its closest prior art analogue (i.e 2,2,5/6,8a-tetramethyl-3,4,4a,5,8, 8a-hexahydro-1(2H)-naphthalenone) by having a totally different odor character.

Another example is 2,2,3α,8aα-tetramethyl-3,4,4aα,5,8, 8a-hexahydro-1(2H)-naphthalenone which possesses a woody aromatic, sage-laurel odor and distinguishes itself from its closest prior art analogue (i.e 2,2,8a-trimethyl-3,4, 4a,5,8,8a-hexahydro-1(2H)-naphthalenone) by having a totally different odor character (e.g. no minty odor).

Finally, one may cite the compound perhydro-2,2,3α,8aα-tetramethyl-4aα-H-1-naphthalenone which possesses a woody aromatic, sage and slightly sulfury odor and distinguishes itself from its closest prior art analogue (i.e perhydro-2,2,8a-trimethyl-4a-H-1-naphthalenone) by having a totally different odor character (e.g. no minty odor).

Therefore, also the compounds of formula (I) or (II) possess different and unexpected odors from the ones of their prior art closest structural analogues.

As mentioned above, the invention concerns also the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in the perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for example, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

Said perfuming co-ingredient is not of the formula (I). Moreover, by "perfuming co-ingredient" it is meant here a compound which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I), as defined above, or an invention's perfuming composition; and
ii) a consumer product base;

is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 25% by weight, or even more, of the compounds of the invention based on the weight of the composition into which they are incorporated. Concentrations lower than these, such as in the order of 0.01% to 10% by weight, can be used when these compounds are incorporated into perfumed articles, percentage being relative to the weight of the article.

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Preparation of the Invention's Compounds

A) 2,3,8a-trimethyl-3,4,4a,5,8,8a-hexahydro-1(2H)-naphthalenone

In a 1 liter round-bottomed flask, at room temperature, were successively added $CH_2Cl_2$ (400 ml), BHT (100 mg) and a 1 M solution of $EtAlCl_2$ in hexanes (80 ml; 0.08 mol). 2,5,6-trimethylcyclohex-2-en-1-one (55.2 g, 0.4 mol, 3:2 mixture of two isomers) was added dropwise, while maintaining the internal temperature below 30° C. Then butadiene (43.2 g, 0.8 mol) was added in one portion. The reaction was stirred at room temperature for 15 days. The reaction was then poured onto cold 5% aqueous HCl and extracted twice with ether. The organic layers were washed with saturated aqueous $NaHCO_3$, water and brine and dried over solid sodium sulfate. The crude product was distilled to give 50 g of a liquid which was then chromatographed on silicagel (heptane:ethyl acetate 49:1) then purified by bulb-to-bulb distillation (B.P.=90° C./0.021 mbar) to give the totle compound (39.43 g, 0.205 mol, 51%) as a 3:2 mixture of diastereoisomers.

MS (major diasereoisomer): 192 (M+, 57); 177 (24); 174 (18); 159 (52); 149 (100); 135 (19); 121 (77); 107 (53); 93 (77); 79 (66); 77 (43).

1H-NMR (mixture of isomers): 0.79 (d, J=7, 1.2 H); 0.96 (d, 1.2 H); 1.01 (d, J=7, 1.8 H); 1.08 (s, 1.2 H); 1.09 (d, J=7, 1.8 H); 1.29 (s, 1.8 H); 1.32-2.2.63 (m, 9 H); 5.50-5.70 (m, 2 H).

B) Perhydro-2,3,8a-trimethyl-1-naphthalenone 2,3,8a-trimethyl-3,4,4a,5,8,8a-hexahydro-1(2H)-naphthalenone (10 g, 52 mmol) was hydrogenated, at room temperature and atmospheric pressure, in ethyl acetate (100 ml) in presence of 5% Pd—C (1.0 g). The crude product was purified by bulb-to-bulb distillation (78° C./0.035 mbar) to give desired compound (9.88 g, 51 mmol, 98%) as a 3:2 mixture of diastereoisomers.

MS (major diasereoisomer): 194 (M+, 19); 179 (11); 161 (6); 152 (42); 139 (100); 109 (18); 95 (35); 81 (33); 67 (21); 55 (16); 41 (16).

1H-NMR(mixture of isomers): 0.72-1.21 (m, 12 H); 1.30-3.00 (m, 10 H).

Example 2

Preparation of the Invention's Compounds

I) General Procedure for the Diels-Alder Coupling

In a 500 ml reactor were introduced the $AlEtCl_2$, or the $AlCl_3$, 0.1 g of BHT and toluene, or $CH_2Cl_2$. Then, under vigorous stirring, was added the appropriate cyclohexenone dropwise, so as to maintain the temperature below 30° C. Afterwards, was added the diene dropwise and when the reaction ended the reaction mixture was hydrolyzed with 5% aqueous HCl, extracted twice with $Et_2O$. The organic layer was then washed with a saturated $NaHCO_3$ aqueous solution, water, brine and then dried over $Na_2SO_4$. Evaporation of the solvents, chromatography ($SiO_2$, elution heptane/AcOEt 98:2) and distillation provided the end product.

2,3,6,8A-Tetramethyl-3,4,4A,5,8,8A-hexahydro-1(2H)-naphthalenone

Prepared with the following quantities:
2,5,6-Trimethyl-2-cyclohexen-1-one (44.16 g, 0.32 mmol)
Aluminium trichloride (10.7 g, 0.08 mmol)
Isoprene (326 g, 4.8 mol)
Toluene (500 ml)

The title compound was obtained as a mixture of isomers (3.5/61.7/1.6/31.5) in 86% yield.

B.p.=42° C./0.005 mbar
$^1H$-NMR: 0.78-1.12 (m, 7 H); 1.22-1.70 (m, 7 H); 1.70-2.62 (m, 7 H); 5.30 (m, 1 H).

2,2,3,8A-Tetramethyl-3,4,4A,5,8,8A-hexahydro-1(2H)-naphthalenone

Prepared with the following quantities:
2,5,6,6-Tetramethyl-2-cyclohexen-1-one (30.4 g, 0.20 mol)
Ethyl aluminium dichloride (1 molar solution in hexanes, 100 ml, 0.10 mol)
Butadiene (40 ml, 0.40 mol)
Dichloromethane (300 ml)
The title compound was obtained in 63% yield.
B.p.=84° C./0.028 mbar $^1$H-NMR: 0.95 (d, J=7 Hz, 3 H); 1.02 (s, 3 H); 1.12 (s, 3H); 1.18 (s, 3 H); 1.50-1.68 (m, 2 H); 1.78-1.88 (m, 2 H); 2.00-2.15 (m, 2 H); 2.20-2.28 (m, 1 H); 2.32-2.42 (m, 1 H); 5.60 (broad s, 2 H).

$^{13}$C-NMR: 219.65 (s); 124.35 (d); 124.01 (d); 46.77 (s); 45.56 (s); 34.95 (d); 33.41 (d); 32.98 (t); 32.04 (t); 28.24 (t); 26.33 (q); 23.30 (q); 21.71 (q); 16.88 (q).

II) General Procedure for the Hydrogenation of the Naphthalenone into the Perhydro Naphthalenone In a 100 ml flask were introduced the appropriate naphthalenone, ethyl acetate and 10% w/w, relative to the naphthalenone, of Pd/C 5%. The mixture was thus stirred under $H_2$, at room temperature, until consumption of the theoretical amount of hydrogen. Afterwards, the reaction mixture was filtered over Nylon 6/6. Evaporation of the solvents and distillation provided the end product.

Perhydro-2,2,3α,8aα-tetramethyl-4aα-H-1-naphthalenone

Prepared from 2,2,3,8A-Tetramethyl-3,4,4A,5,8,8A-hexahydro-1(2H)-naphthalenone in a yield of about 98%.
B.p.=84° C./0.079 mbar

Example 3

Preparation of a Perfuming Composition

A man's "Eau de toilette" was prepared by admixing the following ingredients:

| Ingredient | Parts by weight |
|---|---|
| 1,1-Dimethyl-2-phenylethyl acetate | 10 |
| Geranyl acetate | 10 |
| 10%* 4-(4-Hydroxy-1-phenyl)-2-butanone | 10 |
| Bergamote essential oil | 200 |
| Citral | 30 |
| Lemon essential oil | 500 |
| 2-Methyl-4-(2,2,3-trimethyl-3-cyclopenten-1-yl)-4-penten-1-ol[1] | 80 |
| Habanolide ®[2] | 100 |
| 10%* Galbanum essential oil | 90 |
| Clove-bud | 90 |
| Helvetolide ®[3] | 30 |
| Lavander essential oil | 200 |
| Linalol | 70 |
| Lyral ®[4] | 340 |
| Marjoram | 120 |
| 50%* Oak moss | 50 |
| Cristal Moss | 50 |
| Nutmeg essential oil | 170 |
| 2-Ethoxy-2,6,6-trimethyl-9-methylene-bicyclo[3.3.1]nonane[1] | 170 |
| Cis-3-Hexenol salicylate | 10 |
| Sandela ®[5] | 180 |
| Sclareolate ®[6] | 420 |
| Ylang Extra | 100 |
| | 3030 |

*in dipropyleneglycol
[1] origin: Firmenich SA, Geneva, Switzerland
[2] Pentadecenolide; origin: Firmenich SA, Geneva, Switzerland
[3] (1S,1'R)-2-[1-(3',3'-dimethyl-1'-cyclohexyl)ethoxy]-2-methylpropyl propanoate; origin: Firmenich SA, Geneva, Switzerland
[4] 4/3-(4-Hydroxy-4-methylpentyl)-3-cyclohexene-1-carbaldehyde; origin: International Flavors & Fragrances, USA
[5] 2(4)-(5,5,6-Trimethylbicyclo[2.2.1]hept-2-yl)-1-cyclohexanol; origin: Givaudan-Roure SA, Vernier, Switzerland
[6] Propyl (S)-2-(1,1-dimethylpropoxy)propanoate; origin: Firmenich SA, Geneva, Switzerland The addition of 700 parts by weight of perhydro-2,3,8a-trimethyl-1-naphthalenone to the above-described Eau de toilette imparted to the fragrance of the latter a nice and strong woody-damascone aspect while boosting the freshness of the scent. Furthermore, this fresh woody-damascony note was well perceivable up to the bottom notes, effect not obtainable by the addition of the known synthetic perfuming ingredients known as having a woody character.

The addition of the same amount of perhydro-2,2,8a-trimethyl-1-naphthalenone imparted a much weaker effect, devoid of the damascone, watery fresh effect. The overall impression was that of a much drier and heavy fragrance with a minty note and a patchouli-classic under note having a poor volume.

The invention claimed is:

1. A compound of formula (II):

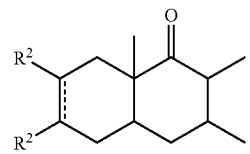

(II)

wherein the dotted line represents a single or double bond and one $R^2$ is a hydrogen atom and the other is a hydrogen atom or a methyl group.

2. A compound according to claim 1, wherein said compound is of formula (III):

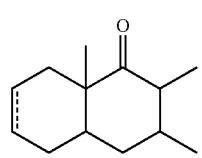

(III)

wherein the dotted line represents a single or double bond.

3. A method to confer, enhance, improve or modify the odor properties of a perfuming composition or of a perfumed article, which method comprises adding to said composition or article an effective amount of at least a compound of claim 1.

4. The method according to claim 3, wherein the compound is of formula (III):

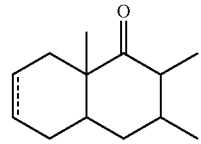

(III)

wherein the dotted line represents a single or double bond.

5. The method according to claim 3, wherein the compound is perhydro-2,3,8a-trimethyl-1-naphthalenone.

6. A perfuming ingredient in the form of a composition comprising:
i) at least a compound of claim 1;
ii) at least one ingredient selected from the group consisting of a perfumery carrier and a perfumery base; and
iii) optionally at least one perfumery adjuvant.

7. The perfuming ingredient according to claim 6, wherein the compound is of formula

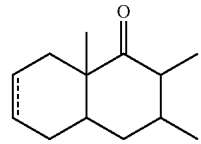

(III)

wherein the doffed line represents a single or double bond.

8. The perfuming ingredient according to claim 6, wherein the compound is perhydro-2,3,8a-trimethyl-1-naphthalenone.

9. A perfumed article comprising:
i) at least a compound of claim 1; and
ii) a consumer product base.

10. The perfumed article according to claim 9, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

11. The perfumed article according to claim 10, wherein the compound is of formula (III):

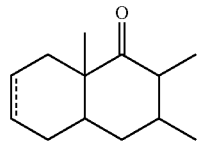

(III)

wherein the dotted line represents a single or double bond.

12. The perfumed article according to claim 10, wherein the compound is perhydro-2,3,8a-trimethyl-1-naphthalenone.

13. Perhydro-2,3,8a-trimethyl-1-naphthalenone.

* * * * *

UNITED STATES PATENT AND TRADEMARK OFFICE
CERTIFICATE OF CORRECTION

PATENT NO. : 7,704,933 B2
APPLICATION NO. : 11/996924
DATED : April 27, 2010
INVENTOR(S) : Moretti et al.

It is certified that error appears in the above-identified patent and that said Letters Patent is hereby corrected as shown below:

Column 9:
Last line (claim 7, last line), delete "doffed" and insert -- dotted --.

Signed and Sealed this

First Day of June, 2010

David J. Kappos
*Director of the United States Patent and Trademark Office*